(12) United States Patent
Hazra et al.

(10) Patent No.: US 7,977,454 B2
(45) Date of Patent: Jul. 12, 2011

(54) PREPARATION OF INSULIN CONJUGATES

(75) Inventors: Partha Hazra, Karnataka (IN);
Manjunath Hadavanahalli Shivarudraiah, Karnataka (IN); Anand Khedkar, Karnataka (IN); Harish Iyer, Karnataka (IN); Nitesh Dave, Karnataka (IN); Gautam Krishnan, Karnataka (IN); Shrikumar Suryanarayan, Karnataka (IN)

(73) Assignee: Biocon Limited, Karnataka (IN)

( * ) Notice: Subject to any disclaimer, the term of this patent is extended or adjusted under 35 U.S.C. 154(b) by 405 days.

(21) Appl. No.: 11/995,059

(22) PCT Filed: Jul. 8, 2005

(86) PCT No.: PCT/IN2005/000234
§ 371 (c)(1),
(2), (4) Date: Jan. 8, 2008

(87) PCT Pub. No.: WO2007/007345
PCT Pub. Date: Jan. 18, 2007

(65) Prior Publication Data
US 2008/0139784 A1    Jun. 12, 2008

(51) Int. Cl.
*C07K 1/107* (2006.01)
*C07K 1/02* (2006.01)
*C07K 1/12* (2006.01)
(52) U.S. Cl. ......................................... 530/303; 530/345
(58) Field of Classification Search ...................... None
See application file for complete search history.

(56) References Cited

U.S. PATENT DOCUMENTS

| | | | |
|---|---|---|---|
| 4,179,337 A | 12/1979 | Davis et al. | |
| 4,343,898 A * | 8/1982 | Markussen | 435/68.1 |
| 5,359,030 A | 10/1994 | Ekwuribe et al. | |
| 6,309,633 B1 | 10/2001 | Ekwuribe et al. | |
| 6,828,297 B2 | 12/2004 | Ekwuribe et al. | |
| 7,166,571 B2 * | 1/2007 | Soltero et al. | 514/3 |

* cited by examiner

*Primary Examiner* — Jeffrey Stucker
*Assistant Examiner* — Daniel C Gamett
(74) *Attorney, Agent, or Firm* — Banner & Witcoff, Ltd.

(57) ABSTRACT

The present invention discloses a process for making an insulin-oligomer conjugate as a one-pot reaction by conjugation of insulin-ester with an activated oligomer wherein simultaneous deblocking and conjugation is carried out.

11 Claims, No Drawings

PREPARATION OF INSULIN CONJUGATES

FIELD OF THE INVENTION

The present invention relates to a process for making an insulin-oligomer conjugate as a one-pot reaction by conjugation of insulin-ester with an activated oligomer wherein simultaneous deblocking and conjugation is carried out.

BACKGROUND OF THE INVENTION

The β-cells of the pancreatic islets secrete a single chain precursor of insulin, known as pro-insulin which upon proteolysis results in the biologically active polypeptide insulin. The insulin molecule is a highly conserved across species and generally consists of two chains of amino acids linked by disulfide bonds. The natural human insulin molecule (mw 5,807 Daltons), has A-chain of 21 amino acid residues with glycine at the amino terminus; and a B-chain of 30 amino acid residues with phenylalanine at the amino terminus. Insulin may exist as a monomer or may aggregate into a dimer or a hexamer formed from three of the dimers. The monomer has the ability to bind to receptors and is the biologically active form.

Insulin polypeptide is the primary hormone responsible for controlling the transport, utilization and storage of glucose in the body. A defect in the carbohydrate metabolism as a result of insufficient production of insulin or reduced sensitivity of the receptor to insulin leads to the biological disorder diabetes. Diabetes impairs the normal ability to use glucose as a result increases blood sugar levels (hyperglycemia). As glucose accumulates in the blood, excess levels of sugar are excreted in the urine (glycosuria). Other symptoms of diabetes include increased urinary volume and frequency, thirst, itching, hunger, weight loss, and weakness. Diabetes when left untreated leads to ketosis, followed by acidosis with nausea and vomiting. As the toxic products continue to build up, the patient goes into a diabetic coma, which leads to the patient's death. There are two types of diabetes. Type I is insulin-dependent diabetes mellitus, or IDDM. IDDM was formerly referred to as "juvenile onset diabetes." In IDDM, insulin is not secreted by the pancreas and must be provided from an external source. Type II or adult-onset diabetes can ordinarily be controlled by diet, although in some advanced cases insulin is required.

Banting et al discloses the use of insulin for treatment for diabetes using active extract from the pancreas in diabetic dogs "Pancreatic Extracts in the Treatment of Diabetes Mellitus" (Can. Med. Assoc. J., 12:141-146 (1922). In that same year, treatment of a diabetic patient with pancreatic extracts resulted in a dramatic, life-saving clinical improvement.

Traditionally bovine and porcine insulin were used almost exclusively to treat diabetes in humans. With the development of recombinant technology commercial scale manufacture of human insulin was made possible by fermentation. Furthermore, genetically engineered insulin analogs having biological activity comparable to that of natural human insulin were developed to combat the disease.

However, treatment of diabetes typically requires regular injections of insulin. Due to the inconvenience of insulin injections, various approaches have been attempted to formulate insulin for administration by non-injectable routes. A list of such disclosures include: U.S. Pat. No. 4,338,306 (Kitao et al.) discloses a pharmaceutical compositions of insulin and fatty acids having 8 to 14 carbon atoms and nontoxic salts thereof for rectal administration of insulin; U.S. Pat. No. 4,579,730 (Kidron et al) discloses an enterocoated insulin compositions with a bile acid or alkali metal salt thereof for the oral administration of insulin; U.S. Pat. No. 5,283,236 (Chiou et al.) discloses an insulin composition with a permeation-enhancing agent to aid systemic absorption of higher molecular weight polypeptides, as well as peptidase inhibitors for systemic delivery of insulin through the eyes wherein the drug passes into the nasolacrimal duct and becomes absorbed into circulation; U.S. Pat. No. 5,658,878 (Backstrom et al.) discloses an insulin and sodium salt of a saturated fatty acid of carbon chain length 10 (i.e., sodium caprate), 12 (sodium laurate), or 14 (sodium myristate) which enhances the absorption of insulin in the lower respiratory tract; U.S. Pat. No. 5,853,748 (New et al.) discloses an enteric-coated composition of insulin, a bile salt or bile acid, and carbonate or bicarbonate ions, used to adjust the pH of the gut to a pH of from 7.5 to 9 for the oral administration of insulin. U.S. Pat. No. 6,200,602 (Watts et al) discloses a drug delivery composition of insulin for colonic delivery of insulin with an absorption promoter which includes a mixture of fatty acids having 6 to 16 carbon atoms and its salts or a mixture of mono/diglycerides of medium chain fatty acids along with a dispersing agent, in a coating to prevent the release of the insulin and absorption promoter until the tablet, capsule or pellet reaches the proximal colon.

Attempts have been made to deliver insulin by oral administration. The problems associated with oral administration of insulin to achieve euglycemia in diabetic patients are well documented in pharmaceutical and medical literature. Digestive enzymes in the GI tract rapidly degrade insulin, resulting in biologically inactive breakdown products. In the stomach, for example, orally administered insulin undergoes enzymatic proteolysis and acidic degradation. Survival in the intestine is hindered by excessive proteolysis. In the lumen, insulin is barraged by a variety of enzymes including gastric and pancreatic enzymes, exo- and endopeptidases, and brush border peptidases. Even if insulin survives this enzymatic attack, the biological barriers that must be traversed before insulin can reach its receptors in vivo may limit oral administration of insulin. For example, insulin may possess low membrane permeability, limiting its ability to pass from the lumen into the bloodstream.

Pharmaceutically active polypeptides such as insulin have been conjugated with polydispersed mixtures of polyethylene glycol or polydispersed mixtures of polyethylene glycol containing polymers to provide polydispersed mixtures of drug-oligomer conjugates; U.S. Pat. No. 4,179,337 (Davis et al) discloses conjugating polypeptides such as insulin with various polyethylene glycols such as MPEG-1900 and M PEG-5000 supplied by Union Carbide. U.S. Pat. No. 5,567,422 (Greenwald) discloses the conjugation of biologically active nucleophiles with polyethylene glycols such as m-PEG-OH (Union Carbide), which has a number average molecular weight of 5,000 Daltons.

Conjugation of polypeptides such as insulin with polyethylene glycol modified glycolipid polymers and polyethylene glycol modified fatty acid polymers are disclosed in U.S. Pat. No. 5,359,030 (Ekwuribe et al.).

U.S. Pat. No. 6,011,008 (Domb et al.) discloses a method for producing a water-soluble polysaccharide conjugate of an oxidation-sensitive substance comprising activating the polysaccharide to a dialdehyde by periodate oxidation; (b) purifying the dialdehyde from interfering anions and by-products; and (c) coupling the substance to the purified dialdehyde by Schiff base formation to form the conjugate. Optionally, the conjugate of step (c) is reduced to an amine conjugate by a reducing substance. Insulin was conjugated to oxidized AG (arabinogalactan) via an amine or imine bond by reacting a solution of pure oxidized AG (arabinogalactan) in borate buffer solution at pH 8.9 with insulin at 4° C. overnight. The clear solution was dialyzed through a cellulose dialysis and the solution was lyophilized to yield 115 mg of a white solid.

U.S. Pat. No. 6,022,524 (Maisano et al.) Gd-DTPA was conjugated with porcine insulin in a solution of DTPA and dimethylsulfoxide (DMSO) is prepared by heating and stirring, then it is cooled at room temperature and added with a solution of 11.73 g NHS (0.102 mol) in 300 ml DMSO, then, drop by drop, with a solution of 19.6 g of N,N'-dicyclohexylcarbodiimide (0.097 mol) in 400 ml DMSO. The mixture is stirred for 16 hours, then filtered and the filtrate is concentrated by evaporation at 50.degree. C. and 5 Pa to a thick oil of an about 160 ml volume.

U.S. Pat. No. 6,309,633 (Ekwuribe et al.) disclose use of solid insulin for conjugation of insulin with laurate $PEG_5$ in presence of Triethylamine and DMSO at room temperature. The reaction was monitored via HPLC every 30 mins. The conjugate was purified using a preparative HPLC.

U.S. Pat. No. 6,828,297 (Ekwuribe et al.) discloses methods for making PEG7-Hexyl-Insulin by using zinc or zinc free human insulin for conjugation with activated oligomer and purification of B29 modified PEG7-Hexyl-Insulin. Insulin in dimethylsulfoxide and triethyl amine was reacted with activated oligomer at 22+/−4° C. The crude reaction mixture is dialyzed or difiltered to remove organic solvents and small molecular weight impurities, exchanged against ammonium acetate buffer and lyophilized; which is further subjected to RP-HPLC equilibrated with 0.5% triethylamine/0.5% phosphoric acid buffer (TEAP A). The column was eluted with a gradient flow using TEAP A and TEAP B (80% acetonitrile and 20% TEAP A) solvent system. Fractions containing the conjugate were pooled and the elution buffer and solvent were removed by dialysis or diafiltration against ammonium acetate buffer and lyophilized to produce white powder of PEG7-hexyl-insulin, B29 monoconjugate (purity>97%).

Currently, existing prior art teaches use of pure insulin powder or crystals as the starting material for making conjugated insulin wherein the insulin used is a biologically active form.

The instant invention facilitates the conjugation of insulin in its inactive ester form with an oligomer wherein the insulin ester is deblocked and conjugated to the oligomer simultaneously as a one pot reaction.

The instant invention is a more simplified and economical in the making of an insulin conjugate wherein several steps of purification to obtain pure insulin in biologically active form are circumvented. The starting material is the fermented broth containing insulin precursor. The broth containing the insulin precursor is subjected to a combination step of Cation exchange purification, crystallization with phenol and $ZnCl_2$, lyophilization, and transpeptidation to obtain insulin ester. The insulin-ester is subjected to conjugation with an oligomer having the general formula —OC—$(CH_2)_n$—$(OCH_2CH_2)_n$—$OCH_3$ and more preferably an activated oligomer of molecular formula $C_{14}H_{23}NO_8$ (CAS.no.622405-78-1), to obtain conjugated insulin. The most preferred insulin-oligomer conjugate is insulin-OC—$CH_2CH_2$—$(OCH_2CH_2)_3$—$OCH_3$ herein after also referred to as IN 105. The overall cost of production of conjugated insulin as a result of this process is minimized.

SUMMARY OF THE INVENTION

The instant invention relates to a process for making an insulin-oligomer conjugate in a one-pot reaction by conjugation of insulin-ester with an activated oligomer wherein simultaneous deblocking and conjugation is done in borate buffer. The activated oligomer solubilized in acetonitrile is added to a solution containing insulin-ester and the pH of the mixture is raised to about 11.

DETAILED DESCRIPTION

The instant invention discloses a one-pot reaction process for the preparation of insulin-oligomer conjugates comprising simultaneous deblocking and conjugation of an insulin-ester.

The insulin-oligomer conjugate is further purified and lyophilized to a dry powder.

The process for making a insulin-oligomer conjugate in one pot comprising:
  (i) transpeptidation of insulin precursor,
  (ii) deblocking of insulin ester and conjugation with an oligomer simultaneously in one pot,
  (iii) affording insulin-oligomer conjugate.

The process further comprising:
  (i) purification of insulin precursor by chromatography and precipitation,
  (ii) transpeptidation to afford an insulin ester,
  (iii) purification of the insulin ester using RP-HPLC,
  (iv) treatment of the insulin ester with an oligomer in borate buffer, to effect deblocking and conjugation simultaneously,
  (v) optional purification of the conjugate,
  (vi) affording insulin-oligomer conjugate.

The process wherein the preparation of insulin-oligomer conjugates comprises one-pot process of deblocking of insulin-ester and conjugation with the oligomer.

The process of making an insulin-oligomer conjugate comprising of simultaneous addition an oligomer solubilized in acetonitrile to a solution containing insulin-ester in borate buffer and increasing the pH of the mixture.

The process wherein the pH is increased to about 11.

The process wherein the insulin precursor is proinsulin or mini-proinsulin.

The process wherein the oligomer is an alkyl-PEG or derivative thereof.

The process wherein the oligomer is activated before conjugation.

The process wherein the activated oligomer used for conjugation is $C_{14}H_{23}NO_8$.

The process wherein the alkyl-PEG has the general formula —OC—$(CH_2)_n$—$(OCH_2CH_2)_n$—$OCH_3$ The process wherein the insulin-oligomer conjugate is insulin B29 Nε-oligomer conjugate.

The process wherein the insulin-alkyl PEG conjugate is insulin B29 Nε-alkyl PEG conjugate.

The process of wherein the conjugate is insulin —OC—$CH_2$—$CH_2$—$(OCH_2CH_2)_3$—$OCH_3$.

Fermentation of Recombinant Yeast Containing the Insulin Gene.

Inoculum of recombinant yeast containing the insulin gene is prepared by adding 100 micro litre glycerol stock culture into 50 ml of minimal glycerol (MGY) medium in 250 ml shake flasks. MGY medium contains yeast nitrogen base (YNB), glycerol, phosphate buffer and D-biotin. Seed flasks are incubated at 30 deg C., 240+/−10 until 15+/−5 OD (optical density at 600 nm) is reached.

Fermentation media contains ortho-phosphoric acid, calcium sulfate di-hydrated, potassium sulfate, magnesium sulfate hepta hydrated, potassium hydroxide, glycerol, trace salts and D-biotin. Fermentor is prepared by adding all the above components except trace salts and D-biotin and autoclaved at 121-124° C. for one hour. Trace salts solution is prepared by filter sterilizing solution of Cupric sulfate penta hydrated, Sodium iodide, Manganese sulfate mono hydrated, Sodium molybdate di hydrated, Boric acid, Cobalt chloride hexa hydrated, Zinc chloride, Ferrous sulfate hepta hydrated. Biotin solution is also filter sterilized. Fermentor is inoculated and run at temperature 30° C., pH 5.5, air flow 0.5 lpm and DO 30. After batch phase, glycerol feed (50% w/w with water) is started to build the biomass. 50% glycerol w/w is prepared and autoclaved for 30 min at 121-124 deg C. and then Trace salts & Biotin solutions are added at the rate of 12 ml/l. Glycerol feed rate is gradually increased up to 20+/−5 g/hr. Once the 300-400 g/l biomass is achieved, temperature is reduced to 20-25° C., pH is changed to 3.5-6.5 and methanol feed is started. Methanol is filter sterilized and trace salt and biotin solutions are added at the rate of 12 g/l. Methanol feed is increased based on consumption up to 25+/−5 g/h. During Methanol feeding yeast extract and peptone feed is added at the rate of 0.2-0.5 g/h. Fermentation is continued up to 12 days.

Purification of Proinsulin from Broth 900 mg of broth containing Insulin Precursor was adjusted to pH 4.0 by acetic acid and passed through the Cation exchange resins, pre equilibrated with the 50 mM acetic acid. The column was washed with 50 mM acetic acid and eluted with 50 mM acetic acid with 1 M NaCl. 855 mg of product was obtained which was diluted 1:3 with water and concentration was made to 6 mg/ml. Phenol was added (1.25 mg/lit) and 5% (v/v) ZnCl2 of 5% (w/v) stock was added to the solution. pH of the solution was adjusted to 5.2 with 1N NaOH. The solution was kept overnight at 4° C. The solid suspension was centrifuged and the pellet formed was lyophilized to dryness. Recovery in the step was 90%.

Transpeptidation and Esterification of the Proinsulin 400 mg of dry precursor powder was solubilized in 30 ml of DMF containing 30-70% N—N Dimethyl formamide. 724 mg of Threonine butyl ester was added to the solution. pH of the solution was adjusted to 6.5 with 3 N Acetic acid. The reaction was started with addition of 55 mg of Trypsin. The reaction was monitored in each hour and was stopped with 5 ml of 3 N acetic acid after 4 hr when the conversion of Insulin precursor to Insulin ester was 74%. Yield of this step was 68% in terms of product conversion.

The product obtained was precipitated as above, at pH 6.0 and 228 mg of Insulin ester was recovered. The crystal pellet of Insulin ester was solubilized in 250 mM acetic acid. The filtered material was passed through C8 Kromasil matrix and the 95% pure Insulin ester was recovered from the acetonitrile gradient. At the end of RPHPLC 149 mg of product was recovered.

The insulin ester so obtained in used for the preparation of the insulin conjugate as disclosed in the following examples; not to be considered as limiting.

EXAMPLES

Example 1

5 ml of the RP elution pool obtained as of example 2 is taken and 1.2 ml of 1 M Borate buffer added to the reaction mixture; pH of the reaction mixtures were raised to 11 and the reaction mixture was stirred for 3 hr at 24° C. Deblocking was monitored and when it was completed, 0.5 mg of the activated oligomer ($C_{14}H_{23}NO_8$) solubilized in 300 μl of Acetonitrile was added to the reaction mixture. The reaction was stopped by bringing down the pH of the reaction to 7.5. The yield is 44%, with a chromatogram purity of 28%. Most of the product remains unconverted.

Example 2

5 ml of RP elution pool is taken as the starting material taken and 1.2 ml of 1 M Borate buffer added to the reaction mixture; pH of the reaction mixtures were raised to 11 and the reaction mixture was stirred for 3 hr at 24° C. Deblocking was monitored and when it was completed, 2.5 mg of the activated oligomer ($C_{14}H_{23}NO_8$) solubilized in 300 μl of Acetonitrile and added to the reaction mixture. The reaction was stopped by bringing down the pH of the reaction to 7.5. The yield 63% with a chromatographic product purity of 56%.

Example 3

5 ml of RP elution pool is taken as the starting material taken and 1.2 ml of 1 M Borate buffer added to the reaction mixture; pH of the reaction mixtures were raised to 11 and the reaction mixture was stirred for 3 hr at 24° C. Deblocking was monitored and when it was completed, 10 mg of the activated oligomer ($C_{14}H_{23}NO_8$) solubilized in 300 μl of Acetonitrile. The sample was analyzed firm all the sets at 10 mins and 1 hr. The yield is 18% with a chromatographic product purity of 11%. Mostly the diconjugated product was observed.

Example 4

5 ml of RP elution pool is taken as the starting material taken and 1.2 ml of 1 M Borate buffer added to the reaction mixture; pH adjusted to 10.5 and kept for 5 hrs. 2.5 mg activated oligomer ($C_{14}H_{23}NO_8$) dissolve in 300 μl of acetonitrile and addled once the DEBLOCKING was completed. Aliquot was taken and analyzed. The yield was 58% with a chromatographic purity of 51%.

Example 5

5 ml of RP elution pool is taken as the starting material taken and 1.2 ml of 1 M Borate buffer added to the reaction mixture; pH adjusted to 10.75 and kept for 4 hrs. 2.5 mg activated oligomer ($C_{14}H_{23}NO_8$) dissolve in 300 μl of acetonitrile and added once the DEBLOCKING was completed. Aliquot was taken and analyzed. The yield was 61% with a chromatographic purity of 53%.

Example 6

Simultaneous Deblocking and Conjugation 5 ml of RP elution pool is taken as the starting material taken and 1.2 ml of 1 M Borate buffer added to the reaction mixture; pH adjusted to 11 and 4 mg activated oligomer ($C_{14}H_{23}NO_8$) dissolved in 300 μl of acetonitrile was added. The sample was analyzed at 10 mins, 1 hr, 2 hrs, 3 hr after simultaneous deblocking with conjugation takes place. The yield 640% with a chromatographic purity of 58%

Example 7

Simultaneous Deblocking and Conjugation 5 ml of RP elution pool is taken as the starting material taken and 1.2 ml of 1 M Borate buffer added to the reaction mixture; pH adjusted to 11 and 2.5 mg activated oligomer ($C_{14}H_{23}NO_8$) dissolved in 300 µl of acetonitrile was added. The sample was analyzed at 10 mins, 1 hr. 2 hr, 3 hr after simultaneous deblocking with conjugation takes place. The yield after 3 hr was 75% with a product purity of 73.4%.

Deblocking continued for 1 hr, 2 hr and 3 hr and Conjugation started in each time point and allowed to continue till both deblocking and conjugation was over for each case.

5 ml each of RP elution pool was taken in each of 4 tubes. 1.2 ml of 1M Borate buffer added to the reaction mixture. pH was adjusted to 11. In the $1^{st}$ Tube 2.5 mg of activated oligomer ($C_{14}H_{23}NO_8$) was added at 0 hr. deblocking was allowed to continue for 1 hr in the $2^{nd}$ tube and same amount of activated oligomer ($C_{14}H_{23}NO_8$) was added to the reaction mixture. Deblocking was allowed to continue for 2 hr in the $3^{rd}$ tube and 2.5 mg of activated oligomer ($C_{14}H_{23}NO_8$) was added after 2 hr. In the $4^{th}$ tube deblocking was continued for 3 hr before same amount of activated oligomer ($C_{14}H_{23}NO_8$) was added. The conjugation was allowed to continue for each tube until it seems to be completed as confirmed by the analytical chromatogram. Yield of the step as well as percentage purity of the insulin conjugate was monitored by analytical chromatograms.

| Experiment # | Yield (%) | Purity of the IN 105 (%) |
|---|---|---|
| Tube 1 | 74.7 | 73.0 |
| Tube 2 | 71.0 | 70.1 |
| Tube 3 | 67.6 | 65.7 |
| Tube 4 | 64.8 | 59.0 |

Example 8

150 ml of RPHPLC elution pool in 36 ml of Borate buffer was taken at pH 8.7. The pH was raised to 11 by adding 10 ml of 10 N NaOH and the reaction mixture was kept at 25° C. for 3 hrs. 135 mg of activated oligomer ($C_{14}H_{23}NO_8$) solubilized in 9 ml of Acetonitrile was added to the reaction mixture to start the Conjugation reaction. After 1 hr, the conjugation reaction was stopped by bringing down the pH of the reaction mixture to 7.5 by adding glacial acetic acid. Yield of deblocking and conjugation was found to be 61% in this reaction and the purity of the product was 62%

Example 9

975 ml of the RP elution pool having concentration of 8.4 mg/ml is taken and 234 ml of 1 M Borate buffer added at pH 8.2. The pH is adjusted to 11 with 10 N NaOH. 975 mg of activated oligomer ($C_{14}H_{23}NO_8$) dissolved in 58.5 ml of acetonitrile was added to the reaction mixture and the deblocking as well as conjugation processes were initiated together.

Aliquot was taken at 2 and 3 hr, analyzed in the HPLC to monitor the reaction profile. The conjugation was stopped after 3 hr by bringing down the pH of the reaction mixture to pH 7.5 by addition of glacial acetic acid. Yield was found to be of 68% with a product purity of 69%.

Example 10

Product Recovery

The end conjugated product is diluted with 250 mM acetic acid to make the concentration of 2.5 mg/ml. The material is loaded on Kromasil C8 RP HPLC column and eluted with acetonitrile gradient. The eluted pool has the IN 105 with a purity of 96.7% and with the recovery in the step of 72%.

The purified IN 105, eluted from the RPHPLC column is crystallized with Phenol and $ZnCl_2$ at pH 5.2 at cold condition. The final crystallized pellet was collected by centrifugation. The collected crystal pellet was lyophilized and collected as dry IN 105 purified crystals.

The invention claimed is:
1. A process for making an insulin-oligomer conjugate in one pot, comprising:
   (i) transpeptidation and esterification of an insulin precursor to provide an insulin ester,
   (ii) deblocking of the insulin ester and conjugation with an oligomer simultaneously in one pot by simultaneous addition of an oligomer solubilized in acetonitrile to a solution containing the insulin-ester in borate buffer and increasing the pH of the solution,
   (iii) obtaining an insulin-oligomer conjugate.
2. A process of claim 1, further comprising:
   (i) purification of insulin precursor by chromatography and precipitation,
   (ii) purification of the insulin ester using RP-HPLC,
   (iii) and optional purification of the conjugate.
3. A process of claim 1, wherein the pH is increased to about 11.
4. A process in claim 1, wherein the insulin precursor is proinsulin or mini-proinsulin.
5. A process in claim 1, wherein the oligomer is an alkyl-PEG or derivative thereof.
6. A process in claim 1, wherein the oligomer is activated before conjugation.
7. A process in claim 6, wherein the activated oligomer used for conjugation is $C_{14}H_{23}NO_8$.
8. A process in claim 5, wherein the alkyl-PEG has the general formula —OC—$(CH_2)_n$—$(OCH_2CH_2)_n$—$OCH_3$.
9. A process of claim 1, wherein the insulin-oligomer conjugate is insulin B29 Nϵ-oligomer conjugate.
10. A process of claim 1, wherein the insulin-oligomer conjugate is insulin B29 Nϵ-alkyl PEG conjugate.
11. A process of claim 1, wherein the conjugate is insulin B29 Nϵ-OC—$CH_2$—$CH_2$—$(OCH_2CH_2)_3$—$OCH_3$.

* * * * *